United States Patent [19]
Thomas

[11] Patent Number: 5,955,460
[45] Date of Patent: Sep. 21, 1999

[54] OXAZOLIDINONE ANTIBACTERIAL AGENT WITH TRICYCLIC SUBSTITUENTS

[75] Inventor: Richard Charles Thomas, Kalamazoo, Mich.

[73] Assignee: Pharmacia & Upjohn Company, Kalamazoo, Mich.

[21] Appl. No.: 09/250,382

[22] Filed: Feb. 15, 1999

Related U.S. Application Data

[62] Division of application No. 08/850,424, May 2, 1997, which is a continuation of application No. 08/744,519, Nov. 5, 1996, abandoned
[60] Provisional application No. 60/007,371, Nov. 17, 1995.

[51] Int. Cl.⁶ .................... C07D 513/04; A61K 31/54
[52] U.S. Cl. .................... 514/224.5; 544/32; 544/34
[58] Field of Search ............. 544/32; 514/224.5

[56] References Cited

FOREIGN PATENT DOCUMENTS 9719089  5/1997  WIPO .

Primary Examiner—Mark L. Berch
Assistant Examiner—Ann Razgunas
Attorney, Agent, or Firm—Lucy X. Yang

[57] ABSTRACT

This invention provides novel oxazolidinone derivatives represented by chemical Formula (I), or pharmaceutically acceptable salts thereof:

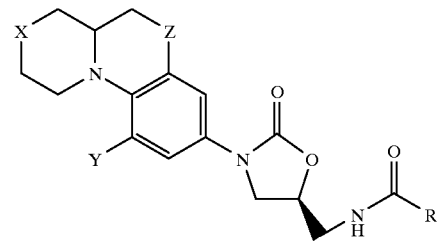

(I)

wherein X is $NR_1$, $CR_2R_3$, O, S, SO, or $SO_2$; and Z is $NR_4$, S, SO, $SO_2$ or O. The compounds are useful antimicrobial agents, effective against a number of human and veterinary pathogens, including gram-positive aerobic bacteria such as multiply-resistant staphylococci and streptococci, as well as anaerobic organisms such as bacteroides and clostridia species, and acid-fast organisms such as *Mycobacterium tuberculosis* and *Mycobacterium avium*.

8 Claims, No Drawings

OXAZOLIDINONE ANTIBACTERIAL AGENT WITH TRICYCLIC SUBSTITUENTS

CROSS-REFERENCE TO RELATED APPLICATION

This application is a divisional application of U.S. Ser. No. 08/850,424, filed May 2, 1997, now pending; which is a continuation of U.S. Ser. No. 08/744,519, filed Nov. 5, 1996, now abandoned; which claims the benefit of provisional application U.S. Ser. No. 60/007,371, filed Nov. 17, 1995, under 35 USC 119(e)(i).

BACKGROUND OF THE INVENTION

1. Field of the Invention

This invention relates to novel oxazolidinone derivatives or pharmaceutically acceptable salts thereof and their preparations. Particularly, this invention relates to oxazolidinone derivatives which are tricyclic fused analogs of the 4-heterocycle-substituted phenyl oxazolidinones.

The compounds are useful antimicrobial agents, effective against a number of human and veterinary pathogens, including gram-positive aerobic bacteria such as multiply-resistant staphylococci and streptococci, as well as anaerobic organisms such as bacteroides and clostridia species, and acid-fast organisms such as *Mycobacterium tuberculosis* and *Mycobacterium avium*.

The compounds are particularly useful because they are effective against the latter organisms which are known to be responsible for infection in persons with AIDS.

2. Information Disclosure

International Publication No. WO 93/23384 discloses oxazolidinones containing a substituted diazine (piperazine) moiety and their uses as antimicrobials.

International Publication No. WO93/09103 discloses substituted aryl and heteroaryl-phenyl-oxazolidinones useful as antimicrobials.

International Publication No. WO95/07271 discloses oxazine and thiazine phenyl-oxazolidinones useful as antimicrobials.

European Patent Publication 609,905 discloses indazolyl, benzimidazolyl, and benzotriazolyl oxazolidinone derivatives useful as antibacterial agents.

U.S. Pat. No. 5,039,690 discloses 5-aminomethyl-N-substituted-oxazolidine derivatives useful as antibacterials active against Gram positive bacteria.

No publications and patents, including the above cited references, were found which disclose tricyclic substituted oxazolidinones.

SUMMARY OF THE INVENTION

This invention provides a novel oxazolidinone derivative represented by the Formula (I):

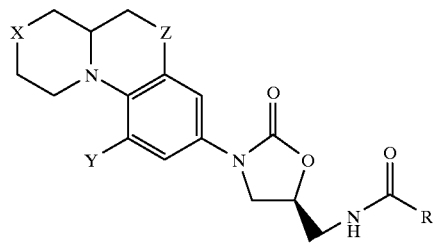

or pharmaceutical acceptable salts thereof wherein
X is
- (a) $NR_1$,
- (b) $CR_2R_3$,
- (c) S, SO, $SO_2$, or
- (d) O;

$R_1$ is
- (a) H,
- (b) $C_{1-6}$ alkyl,
- (c) —$(CH_2)_h$—Aryl,
- (d) —$(CH_2)_h$—C(=O)—$R_{1a}$,
- (e) —C(=O)—$R_{1a}$,
- (f) —C(=O)—$OR_{1a}$,
- (g) —C(=O)—$(CH_2)_h$—C(=O)$R_{1a}$,
- (h) —$SO_2$—$R_{1c}$,
- (i) —(C=O)—Het,
- (j) 2-pyridyl,
- (k) 2-pyrimidinyl,
- (l) 3-pyridazinyl, or
- (m) 2-quinolyl;

$R_{1a}$ is
- (a) H,
- (b) $C_{1-6}$ alkyl,
- (c) Aryl
- (d) —$(CH_2)_h$—Aryl, or
- (e) —$(CH_2)_h$—$OR_{1b}$;

$R_{1b}$ is
- (a) H,
- (b) $C_{1-6}$ alkyl,
- (c) —$(CH_2)_h$—Aryl, or
- (d) —C(=O)—$C_{1-6}$alkyl;

$R_{1c}$ is
- (a) $C_{1-6}$ alkyl, or
- (b) Aryl;

Aryl is phenyl, optionally substituted with one or more of the following
- (a) halogen,
- (b) $C_{1-6}$ alkyl,
- (c) $C_{1-4}$ alkoxy,
- (d) $C_{1-4}$ alkylthio,
- (e) —OH,
- (f) —$NH_2$,
- (g) —SH,
- (f) —$NO_2$, or
- (h) —O—C(=O)—$OCH_3$;

Het is a 5-, 6-, 8-, 9-, or 10-membered heteroaromatic moiety having one or more atoms selected from the group consisting of N, O, and S;

$R_2$ and $R_3$ are each and independently
- (a) H,
- (b) $C_{1-6}$ alkyl,
- (c) $C_{1-6}$ alkoxy,
- (d) $C_{1-4}$ alkylthio, (e) —$(CH_2)_j$—$OR_{2a}$,
(f) —$NR_{2b}R_{3b}$,
(g) —N=CH—$NR_{2c}R_{3c}$,
(h) —C(=O)—$NR_{2b}R_{3b}$,
(i) —$(CH_2)_j$—C(=O)—$R_{2d}$,
(j) —$(CH_2)_j$—Q,
(k) —$(CH_2)_j$—W, or $R_2$ and $R_3$ taken together are
(a) =O,
(b) =$NR_{3d}$,
(c) =S,
(d) =$CR_{2c}R_{3c}$, or
(e) Q;

$R_{2a}$ is
(a) H,
(b) $C_{1-6}$ alkyl,
(c) —$(CH_2)_j$—$OR_{2e}$,
(d) —$(CH_2)_j$—C(=O)—$R_{2d}$,
(e) —C(=O)—$(CH_2)_j$—$OR_{2c}$, or
(f) tosyl;

$R_{2b}$ and $R_{3b}$ are each and independently
(a) H,
(b) —$(CH_2)_j$—$OR_{2e}$,
(c) $C_{1-6}$ alkyl,
(d) —C(=O)—$R_{2d}$,
(e) —C(=O)—$NR_{2e}R_{3e}$,
(f) —$(CH_2)_h$—Aryl, or
(g) —Het;

$R_{2c}$ and $R_{3c}$ are each and independently
(a) H,
(b) $C_{1-6}$ alkyl,
(c) —C(=O)—$R_{2d}$, or
(d) —$(CH_2)_h$—Aryl;

$R_{2d}$ is
(a) H,
(b) hydroxy,
(c) $C_{1-6}$ alkyl,
(d) $C_{1-6}$ alkoxy,
(e) —O—$CH_2$—O—C(=O)—$R_{2e}$, or
(f) —$(CH_2)_j$—C(=O)—$OR_{2e}$;

$R_{3d}$ is
(a) —$OR_{2a}$,
(b) $C_{1-6}$ alkyl,
(c) $C_{1-6}$ alkoxy, or
(d) —$(CH_2)_h$—Aryl;

$R_{2e}$ and $R_{3e}$ are each and independently
(a) H,
(b) $C_{1-6}$ alkyl, or
(c) methoxymethyl;

Q is
a saturated 5-membered heterocyclic moiety having 1–2 atoms selected from the group consisting of N, O, and S;

W is
a saturated 6-membered heterocyclic moiety having 1–2 atoms selected from the group consisting of N, O, and S;

Z is
(a) $NR_4$,
(b) S, SO, $SO_2$, or
(c) O;

$R_4$ is
(a) H,
(b) $C_{1-6}$ alkyl
(c) —C(=O)—$R_{4a}$,
(d) —C(=O)—$OR_{4a}$, or
(e) —C(=O)—$(CH_2)_h$—C(=O)$R_{4a}$;

$R_{4a}$ is
(a) H,
(b) $C_{1-6}$ alkyl,
(c) —$(CH_2)_h$—Aryl, or
(d) —$(CH_2)_h$—$OR_{4b}$;

$R_{4b}$ is
(a) H,
(b) $C_{1-6}$ alkyl, or
(c) —$(CH_2)_h$—Aryl;

Y is
a) H, or
b) halogen;

R is
a) H,
b) $C_{1-4}$ alkyl,
c) $C_{3-6}$ cycloalkyl,
d) $C_{1-4}$ alkoxy,
e) amino,
d) $C_{1-4}$ alkylamino, or
e) $C_{1-4}$ dialkylamino;

h is 1, 2, 3, or 4;

j is 0, or 2; and $C_{1-6}$ alkyl, in each of the above definitions, may be each and independently substituted with one or more halogen, hydroxy, or cyano.

This invention provides novel oxazolidinone derivatives useful as preventatives and therapeutics for infectious diseases. The compounds of this invention have excellent antimicrobial action against various human and veterinary pathogens, including multiply-resistant staphylococci and streptococci, as well as anaerobic organisms such as bacteroides and clostridia species, and acid-fast *Mycobacterium tuberculosis* and *Mycobacterium avium*.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j" inclusive. Thus, $C_{1-4}$ alkyl refers to alkyl of 1–4 carbon atoms, inclusive, or methyl, ethyl, propyl, butyl and isomeric forms thereof.

The term "$C_{1-4}$ alkyl" and "$C_{1-6}$ alkyl" refer to an alkyl group having one to four, or one to six carbon atoms respectively such as, for example, methyl, ethyl, n-propyl, n-butyl, n-pentyl, n-hexyl and isomeric forms thereof, and preferably an alkyl group having 1 to 4 carbon atoms.

The alkyl groups may optionally be substituted by one or more substituents selected from the group consisting of a halogen atom, a hydroxy group, or —CN group such as, for example, fluoromethyl, difluoromethyl, fluoroethyl, cyanomethyl and the like.

The term "$C_{1-4}$ alkoxy" and "$C_{1-6}$ alkoxy" refer to an alkyl group having one to four or one to six carbon atoms respectively attached to an oxygen atom of hydroxy group such as, for example, methoxy, ethyloxy, n-propoxy, n-butyloxy, n-pentyloxy, n-hexyloxy and isomeric forms thereof, and preferably an alkoxy group having one to four carbon atoms.

The term "$C_{1-4}$ alkylthio" and "$C_{1-6}$ alkylthio" refer to an alkyl group having one to four or one to six carbon atoms attached to an thiohydroxy moiety, for example, methythio, ethylthio, propylthio, butylthio, pentylthio, hexylthio and isomeric forms thereof, and preferably an alkylthio group having one to four carbon atoms.

The term "$C_{2-6}$ alkenyl" refers to vinyl, 1-propenyl, 2-propenyl, 2-methyl-1-propenyl, 1-butenyl, 2-butenyl, 1-pentenyl, 2-pentenyl, 1-hexenyl and isomeric forms thereof, and preferably an alkenyl group having two to four carbon atoms.

The term "$C_{3-6}$ cycloalkyl" refers to cyclopropyl, cyclobutyl, cyclopentyl, cyclohexyl and isomeric forms thereof, and preferably an cycloalkyl group having four to six carbon atoms.

The term "$C_{1-4}$ alkylamino" refers to an alkyl group having one to four carbon atoms attached to an amino moiety, for example, methylamine, ethylamine, n-propylamine, n-butylamine, and isomeric forms thereof.

The term "$C_{1-4}$ dialkylamino" refers to two alkyl groups having one to four carbon atoms attached to an amino moiety, for example, dimethylamine, methylethylamine, diethylamine, dipropylamine, methypropylamine, ethylpropylamine, dibutylamine, and isomeric forms thereof.

The term "halogen" refers to fluoro, chloro, bromo, or iodo, preferably fluoro and chloro.

The term "Q" refers to a saturated 5-membered heterocyclic moiety having 1–2 atoms selected from the group consisting of nitrogen, oxygen, and sulfur forming such groups as, for example, dioxolane, imidazolidine, dithiolane, oxathiolane and oxazolidine. A preferred hetero ring within the definition is dioxolane.

The term "W" refers to a saturated 6-membered heterocyclic moiety having 1–2 atoms selected from the group consisting of nitrogen, oxygen, and sulfur forming such groups as, for example, piperidinyl, piperazinyl, morpholino and thiomorpholino; each of which may be substituted by $C_{1-6}$ alkyl or —$(CH_2)_f$—OH. A preferred hetero ring within the definition is morpholino.

The term "Het" refers to a 5-, 6-, 8-, 9-, or 10-membered heteroaromatic moiety having one or more atoms selected form the group consisting of nitrogen, oxygen, and sulfur forming such groups as, for example, pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-indolyl, 3-indolyl, 3-indazolyl, 2-benzoxazolyl, 2-benzothiazolyl, 2-benzimidazolyl, 2-benzofuranyl, 3-benzofuranyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-1,2,4-triazol-1-yl, 1-tetrazolyl, 1-indolyl, 1-indazolyl, 2-isoindolyl, 1-purinyl, 3-isothiazolyl, 4-isothiazolyl and 5-isothiazolyl. A preferred heteroaromatic ring within the definition is 2-thiazolyl, 1,2,4-triazol-4-yl, 2-indolyl or 5-isoxazolyl.

Within the definition of the terms "Het", "Q" and "W", the nitrogen atom forming the hetero rings may have a protective group such as an acetyl or hydroxyacetyl group.

The compounds of the present invention can be converted to their salts according to conventional methods.

The term "pharmaceutically acceptable salts" refers to salts useful for administering the compounds of this invention and these include hydrochloride, hydrobromide, hydroiodide, sulfate, phosphate, acetate, propionate, lactate, mesylate, maleate, malate, succinate, tartrate, citrate, 2-hydroxyethyl sulfonate, fumarate and the like. These salts may be in hydrated form. Some of the compounds of this invention may form metal salts such as sodium, potassium, calcium and magnesium salts and these are embraced by the term "pharmaceutically acceptable salts".

In a preferred embodiment of the N-phenyloxazolidinone compounds of the present invention, the preferred $R_1$ is H, fluoroethyl, cyanomethyl, methyl sulfonyl, formyl, hydroxyacetyl, acetyl, methoxyacetyl, benzyloxyacetyl, acetoxyacetyl, dichloroacetyl, methoxy carbonyl, tert-butoxy carbonyl, benzyloxy carbonyl, 3-hydroxypropionyl, 3-methoxypropionyl, 4-oxopentanoyl, 2-indole carbonyl, 5-isoxazole carbonyl, or 5-nitro-2-thiazoyl, and more preferred $R_1$ is formyl, methoxy carbonyl, hydroxyacetyl, benzyloxyacetyl, 2-indole carbonyl, or 5-isoxazole carbonyl.

The preferred $R_2$ and $R_3$ is when $R_2$ and $R_3$ take together to form =O, or =$NR_{3d}$.

The preferred R is methyl.

The preferred absolute configuration at C-5 of the oxazolidinone ring of compounds claimed in this invention is as represented in the structure of Formula (I). This absolute configuration is called (S) under the Cahn-Ingold-Prelog nomenclature system. It is this (S)-enantiomer which is pharmacologically active. The racemic mixture is useful in the same way and for the same purpose as the pure (S)-enantiomer; the difference is that twice as much racemic material must be used to produce the same antibacterial effect. Depending on substituents, the compounds of this invention may exist in geometric, optical and other isomeric forms and this invention embraces any of these isomers or enantiomers Particular preferred examples of the oxazolidinone derivatives represented by the general Formula (I) are as follows (prefixed by compound numbers):

1. 8-[5-(S)-[(Acetylamino)methyl]-2-oxo-3-oxazolidinyl]-1,2,4a,5-tetrahydropyrazino[2,1-c][1,4]benzoxazine-3 (4H)-carboxylic acid phenylmethyl ester, 2. N-[[3-[1,2,3,4,4a,5-Hexahydro-3-[(phenylmethoxy) acetyl]pyrazino[2,1-c][1,4]benzoxazin-8-yl]-2-oxo-5-(S)-oxazolidinyl]methyl]-acetamide, 3. 8-[5-(S)-[(Acetylamino)methyl]-2-oxo-3-oxazolidinyl]-1,2,4a,5-tetrahydropyrazino[2,1-c][1,4]benzoxazine-3 (4H)-carboxylic acid methyl ester, 4. N-[[3-[1,2,3,4,4a,5-Hexahydro-3-(hydroxyacetyl) pyrazino[2,1-c][1,4]benzoxazin-8-yl]-2-oxo-5-(S)-oxazolidinyl]methylacetamide, 5. N-[[3-[1,2,3,4,4a,5-Hexahydro-3-(5-isoxazolylcarbonyl) pyrazino[2,1-c][1,4]benzoxazin-8-yl]-2-oxo-5-(S)-oxazolidinyl]methyl]-acetamide, 6. N-[[3-[1,2,3,4,4a,5-Hexahydro-3-(1H-indol-2-ylcarbonyl)pyrazino[2,1-c][1,4]benzoxazin-8-yl]-2-oxo-5-(S)-oxazolidinyl]methyl]-acetamide, 7. N-[[3-[1,2,3,4,4a,5-hexahydropyrazino[2,1-c][1,4] benzoxazin-8-yl]-2-oxo-5-(S)-oxazolidinyl]methyl]-acetamide, 8. N-[[3-[1,2,3,4,4a,5-hexahydro-3-(2-fluoroethyl)pyrazino [2,1-c][1,4]benzoxazin-8-yl]-2-oxo-5-(S)-oxazolidinyl] methyl]-acetamide, 9. N-[[3-[1,2,3,4,4a,5-hexahydro-3-(cyanomethyl)pyrazino [2,1-c][1,4]benzoxazin-8-yl]-2-oxo-5-(S)-oxazolidinyl] methyl]-acetamide, 10. N-[[3-[1,2,3,4,4a,5-hexahydro-3-(methylsulfonyl) pyrazino[2,1-c][1,4]benzoxazin-8-yl]-2-oxo-5-(S)-oxazolidinyl]methyl]-acetamide,
11. N-[[3-[1,2,3,4,4a,5-hexahydro-3-(formyl)pyrazino[2,1-c][1,4]benzoxazin-8-yl]-2-oxo-5-(S)-oxazolidinyl] methyl]-acetamide,
12. N-[[3-[1,2,3,4,4a,5-hexahydro-3-(acetyl)pyrazino[2,1-c][1,4]benzoxazin-8-yl]-2-oxo-5-(S)-oxazolidinyl]methyl]-acetamide,
13. N-[[3-[1,2,3,4,4a,5-hexahydro-3-(methoxyacetyl) pyrazino[2,1-c][1,4]benzoxazin-8-yl]-2-oxo-5-(S)-oxazolidinyl]methyl]-acetamide,
14. N-[[3-[1,2,3,4,4a,5-hexahydro-3-(acetoxyacetyl) pyrazino[2,1-c][1,4]benzoxazin-8-yl]-2-oxo-5-(S)-oxazolidinyl]methyl]-acetamide,
15. N-[[3-[1,2,3,4,4a,5-hexahydro-3-(dichloroacetyl) pyrazino[2,1-c][1,4]benzoxazin-8-yl]-2-oxo-5-(S)-oxazolidinyl]methyl]-acetamide,
16. 8-[5-(S)-[(acetylamino)methyl]-2-oxo-3-oxazolidinyl]-1,2,4a,5-tetrahydropyrazino[2,1-c][1,4]benzoxazine-3 (4H)-carboxylic acid 1,1-dimethylethyl ester,
17. N-[[3-[1,2,3,4,4a,5-hexahydro-3-(3-hydroxypropionyl) pyrazino[2,1-c][1,4]benzoxazin-8-yl]-2-oxo-5-(S)-oxazolidinyl]methyl]-acetamide,
18. N-[[3-[1,2,3,4,4a,5-hexahydro-3-(3-methoxypropionyl) pyrazino[2,1-c][1,4]benzoxazin-8-yl]-2-oxo-5-(S)-oxazolidinyl]methyl]-acetamide,
19. N-[[3-[1,2,3,4,4a,5-hexahydro-3-(4-oxopentanoyl) pyrazino[2,1-c][1,4]benzoxazin-8-yl]-2-oxo-5-(S)-oxazolidinyl]methyl]-acetamide,
20. N-[[3-[1,2,3,4,4a,5-hexahydro-3-(5-nitro-2-thiazoyl) pyrazino[2,1-c][1,4]benzoxazin-8-yl]-2-oxo-5-(S)-oxazolidinyl]methyl]-acetamide,
21. (R)-8-[5-(S)-[(acetylamino)methyl]-2-oxo-3-oxazolidinyl]-1,2,4a,5-tetrahydropyrazino[2,1-c][1,4] benzoxazin-3(4H)-carboxylic acid phenylmethyl ester,
22. (S)-8-[5-(S)-[(acetylamino)methyl]-2-oxo-3-oxazolidinyl]-1,2,4a,5-tetrahydropyrazino[2,1-c][1,4] benzoxazin-3(4H)-carboxylic acid phenylmethyl ester,
23. (R)-8-[5-(S)-[(acetylamino)methyl]-2-oxo-3-oxazolidinyl]-1,2,4a,5-tetrahydropyrazino[2,1-c][1,4] benzoxazine-3(4H)-carboxylic acid methyl ester,
24. (S)-8-[5-(S)-[(acetylamino)methyl]-2-oxo-3-oxazolidinyl]-1,2,4a,5-tetrahydropyrazino[2,1-c][1,4] benzoxazine-3(4H)-carboxylic acid methyl ester,
25. (R)-N-[[[1,2,3,4,4a,5-hexahydropyridino[2,1-c][1,4] benzoxazin-8-yl]-2-oxo-5-(S)-oxazolidinyl]methyl]-acetamide, and
26. (S)-N-[[[1,2,3,4,4a,5-hexahydropyridino[2,1-c][1,4] benzoxazin-8-yl]-2-oxo-5-(S)-oxazolidinyl]methyl]-acetamide.

The compounds represented by the general formula (I) can be prepared by the method of reactions in Schemes I, II, III and IV.

As shown in Scheme I, structure 1 is reacted with difluoronitrobenzene 2 (Y=hydrogen or halogen) in the presence of a suitable base such as dipotassium hydrogenphosphate, sodium hydride or N,N-diisopropylethylamine, and in a suitable solvent such as dimethyl sulfoxide (DMSO), acetonitrile, tetrahydrofuran (THF), ethyl acetate, or dimethyl formamide (DMF) at room temperature or reflux temperature to provide the adduct 3. All of the starting compounds of structure 1 can be prepared by procedures well known to one of ordinary skill in organic chemistry. The following publications further describe and exemplify these procedures: Asher, V. et al., Tetrahedron Letters Vol. 22, pp 141–144 (1981); Kogami, Y. and Okawa, K, Bull. Chem. Soc. Jpn., Vol. 60, pp 2963–1965 (1987); Naylor, A. et al., J. Med. Chem. Vol. 36, pp 2075–2083 (1993); Brown, G. R. et al., J. Chem. Soc. Perkin Trans. I pp 2577–2580 (1985). The treatment of structure 3 with a suitable base such as sodium hydride in a suitable solvent such as DMF or DMSO at a suitable temperature in the range −10 to 50° C. provides tricyclic compound 4. The nitro group of structure 4 is then reduced by hydrogenation in the presence of a suitable catalyst such as palladium on carbon or Lindlar catalyst in a suitable solvent such as ethyl acetate, THF, methanol, methylene chloride, chloroform or a mixture thereof. The aniline 5 is then converted to its benzyl urethane derivative 6, employing standard Schotten-Baumann conditions or other means known to one skilled in the art. The urethane 6 is then deprotonated by the action of a suitable base such as n-butyllithium or lithium bis(trimethylsilyl) amide in a suitable solvent such as THF or DMF at a suitable temperature in the range −78 to −40° C. to give a lithiated intermediate which is then treated with commercially available (−)-(R)-glycidyl butyrate. Warming to ambient temperature affords the compound 7 which is the desired enantiomer of hydroxymethyl-substituted oxazolidinone. Compound 7 is then converted to the corresponding mesylate ($R_5$=methyl) or aryl sulfonate ($R_5$=Aryl, for example p-toluenesulfonyl) by reaction with, for example, methanesulfonyl chloride/pyridine or methanesulfonyl chloride/triethylamine/dichloromethane or methanesulfonyl chloride/triethylamine/DMSO or p-toluenesulfonyl chloride/pyridine. The resultant sulfonate derivative 8 is then reacted with sodium azide or potassium azide or the like in a solvent such as DMF or 1-methyl-2-pyrrolidinone optionally in the presence of a catalyst such as 18-crown-6 at a temperature of 50–90° C. to afford an azide intermediate. The azide intermediate is then reduced by hydrogenation with palladium on carbon, Lindlar catalyst or a platinum catalyst in an appropriate solvent such as ethyl acetate, methanol, methylene chloride, chloroform or a mixture thereof to give the corresponding amine 9. Alternatively, the azide can be reduced by reaction with a trivalent phosphorus compound such as triphenylphosphine in a suitable solvent such as THF followed by the addition of water. Alternatively, the amine 9 may be prepared directly from the mesylate 8 by ammonolysis with aqueous ammonium hydroxide in a solvent system consisting of $H_2O$/isopropanol/THF in a sealed reaction vessel immersed at a suitable temperature in the range 70 to 120° C. The amine 9 is then acylated by methods known to those skilled in the art to give oxazolidinones of structure 10. For example, the amine can be reacted with an acid chloride or anhydride in a basic solvent such as pyridine at a temperature ranging from −30 to 30° C. to provide the acylated compound 10.

If desired, structures 3 and 7 can be resolved using chiral HPLC to provide the corresponding diastereomers as illustrated in Examples 7 to 9. The remaining synthetic steps which lead to highly diastereomerically enriched compound 10 are similar to the method as described above.

The compounds of structure 10 represent examples of tricyclic ring substituted oxazolidinone antimicrobial agents of Formula (I) wherein Z is oxygen. Schemes II, III and IV illustrate methods for preparing compounds of Formula (I) wherein Z is nitrogen and sulfur, respectively.

As shown in Scheme II, structure 3 is converted to the corresponding mesylate ($R_5$=methanesulfonyl) or aryl sulfonate ($R_5$=$ArSO_2$, for example p-toluenesulfonyl) by reaction with, for example, methanesulfonyl chloride/pyridine or methanesulfonyl chloride/triethylamine/dichloromethane or methanesulfonyl chloride/triethylamine/DMSO or p-toluenesulfonyl chloride/pyridine. The resultant sulfonate derivative 11 is then reacted with sodium azide or potassium azide or the like in a suitable solvent, optionally in the presence of a catalyst such as 18-crown-6 to afford an azide intermediate. The azide intermediate 12 is then reduced by reaction with a trivalent phosphorus compound such as triphenylphosphine in a suitable solvent such as THF followed by the addition of water to provide the corresponding amine 13. The treatment of structure 13 with a suitable base such as sodium hydride in a suitable solvent such as DMF or DMSO provides tricyclic compound 14. The remaining synthetic steps which lead to the structure 17 of the present invention is similar to that described in Scheme I. Alternatively, catalytic hydrogenation of CBz group of structure 17 in the presence of a suitable metal catalyst provides the corresponding amine, which can be used to make derivatives by reactions known to those skilled in the art such as acylation, alkylation, or alkoxyacylation.

Scheme III illustrates an alternative method for preparing compounds of Formula (I) wherein $Z=NR_4$. Structure 3 is oxidized to the corresponding aldehyde 18 by any of numerous oxidants known in the art such as manganese dioxide. Reductive amination employing a reducing agent such as sodium cyanoborohydride in a suitable solvent such as methyl alcohol or ethyl alcohol and an amine $R_4NH_2$ ($R_4$=H or $C_1$–$C_6$ alkyl) provides structure 19. Base catalyzed ring closure is effected by treatment of 19 with a suitable base such as sodium hydride in a suitable solvent such as DMF or DMSO to provide compound 14 (where R=H) or 20 (where $R_4=C_1$–$C_6$ alkyl). The remaining synthetic steps for conversion of 14 and 20 into the structures 21 are similar to those described in Scheme I. Alternatively, in Scheme III, $R_4$ may be benzyl. Here reduction of the nitro group by catalytic hydrogenation employing a suitable catalyst such as palladium on carbon in a suitable solvent such as methanol results in concomitant removal of the benzyl group to afford compound 15, linking this route with that of Scheme II.

Scheme IV illustrates a method for preparing compounds of Formula (I) wherein Z is sulfur. As shown in Scheme III, the sulfonate derivative 11 is converted to the corresponding thiocarbonic ester 22 ($R_6$ is $C_{1-4}$ alkyl or phenyl) by reaction with a carbothioic acid, for example, ethylthioic acid in the presence of a suitable base. The reduction of the carbonyl group provides the corresponding thio compound 23. The remaining synthetic steps which lead to the structure 25 of the present invention is similar to that described in Scheme I.

When necessary, the side chains of $R_1$, $R_2$ and $R_3$ may be protected during the preparation with a suitable protecting group(s) such as a carbobenzyloxy (CBz), benzyl, or others as described in Greene, T. W.; Wuts, P. G. M. "Protective Groups in Organic Synthesis", 2nd ed., John Wiley & Sons, New York (1991). The protecting groups are optionally removed after the synthesis. A substituent such as amino, hydroxy, ester or carbonyl group in $R_2$ or $R_3$ can be converted to the corresponding derivative such as alkylamide, ether, carboxyl, hydroxyalkyl or oxime group by methods known to those skilled in the art. Also, it will be apparent to one skilled in the art that other acyl groups within the scope of this invention can be readily appended to the amine 9 in Scheme I by standard acylation techniques, for example, those highlighted in March, J. "Advanced Organic Chemistry", 3rd ed., John Wiley & Sons, New York, pp 370–375 (1985), to give additional examples of compound 10. Any appended protecting group on the side chains of $R_1$ on the piperidine ring can be removed employing appropriate conditions such as those noted in Greene, T. W.; Wuts, P. G. M., "Protective Groups in Organic Synthesis," 2nd ed.; John Wiley & Sons, New York (1991). In the case where $R_1$ is hydrogen, the tricyclic ring substituted oxazolidinone of Formula (I) can be used to make derivatives by reactions known to those skilled in the art such as acylation, alkylation, sulfonylation, or alkoxyacylation. Furthermore, in the case where X is sulfur, the sulfur group can be oxidized by an appropriate oxidizer such as N-methylmorpholine N-oxide and osmium tetroxide in an appropriate solvent such as mixtures of water and acetone, or by $NaIO_4$ in an appropriate solvent such as mixtures of water and methanol, to provide the corresponding sulfones and sulfoxides, respectively. In the case where both X and Z are sulfurs, the sulfur group at the X position can be selectively oxidized in an early synthetic step, or both sulfur groups can be oxidized at the end of synthetic step if it is desirable.

These compounds are useful for the treatment of microbial infections in humans and other warm blooded animals by either parenteral, oral, or topical administration.

The pharmaceutical compositions of this invention may be prepared by combining the compounds of Formula (I) of this invention with a solid or liquid pharmaceutically acceptable carrier and, optionally, with pharmaceutically acceptable adjuvants and excipients employing standard and conventional techniques. Solid form compositions includes powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing conventional coloring agents, flavoring agents, stabilizers and thickening agents.

Preferably, the pharmaceutical composition is provided employing conventional techniques in unit dosage form containing effective or appropriate amounts of the active component, that is, the compound of Formula (I) according to this invention.

The quantity of active component, that is the compound of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating, or combatting bacterial infections in humans and other animals that have been diagnosed with bacterial infections, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100 mg/kg, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula (I) according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula (I) as a soluble salt (acid addition salt or base salt) dissolved in a pharmaceutically acceptable liquid carrier such as, for example, water-for-injection and a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine, to name a few. The compound according to Formula (I) generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned antibacterially effective amount of dosage. The compounds of Formula (I) according to this invention are advantageously administered orally in solid and liquid dosage forms.

The compounds of this invention are useful antimicrobial agents, effective against various human and veterinary pathogens, including multiply-resistant staphylococci and streptococci, as well as anaerobic organisms such as bacteroides and clostridia species, and acid-resistant organisms such as *Mycobacterium tuberculosis* and *Mycobacterium avium*. Humans or animals infected with such pathogens are readily diagnosed by a physician or veterinarian of ordinary skill.

Antimicrobial activity was tested in vitro using the procedure described in National Committee for Clinical Laboratory Standards. Methods for dilution antimicrobial susceptibility tests for bacteria that grow aerobically--third edition; Approved Standard. NCCLS Document M7-A3. Villanova, Pa.: NCCLS; 1993. Minimum inhibitory concentration (MIC) values were determined by an agar dilution method (1) in which the test medium was Mueller Hinton agar (MHA; Difco Laboratories, Detroit, Mich.) supplemented with 1% Supplement C (Difco). Serial two-fold dilutions of each compound were prepared using 1.0 ml volumes of sterile distilled water. To each 1.0 ml aliquot was added 9.0 ml of molten agar medium. The drug-supplemented agar was mixed, poured into 15×100 mm petri dishes, and allowed to solidify and dry at room temperature prior to inoculation. The test cultures were grown aerobically overnight at 35° C. on MHA; streptococcal strains were grown on Trypticase Soy Blood Agar Base EH (Difco) supplemented with 5% defibrinated sheep blood (BBL, Becton Dickinson Company, Cockeysville, Md.). Colonies were harvested with a sterile swab, and cell suspensions were prepared in Trypticase Soy Broth (TSB; Becton Dickinson Company) to equal the turbidity of a 0.5 McFarland standard. A 1:19 dilution of the suspension was made in TSB; this diluted suspension constituted the inoculum for the assay. The plates containing the drug-supplemented agar were inoculated with a 0.001 ml drop of the cell suspensions using a Steers replicator (Melrose Machine Shop, Woodlyn, Pa.), yielding approximately $10^4$–$10^5$ cells per spot. The plates were incubated aerobically at 35° C. for 18 hours and the MIC was read as the lowest concentration of drug that inhibited visible growth of the organism. The growth of a single colony was considered to be negative. The data are shown in TABLE 1.

TABLE 1

In Vitro Activity of Compounds Against *Staphylococcus aureus* UC® No. 9213, *Staphylococcus aureus* UC® No. 6685 and *Streptococcus Pneumoniae* UC® No. 9912.

| Example No. | S. a. 9213 (μg/mL) | S. a. 6685 (μg/mL) | S. p. 9912 (μg/mL) |
|---|---|---|---|
| 1 | 8 | 4 | 1 |
| 2 | 8 | 8 | 2 |
| 3 | 8 | 4 | 1 |
| 4 | 8 | 8 | 1 |
| 5 | 4 | 2 | <0.5 |
| 6 | 8 | 4 | 1 |
| 7a | 8 | 4 | 1 |
| 7b | 8 | 8 | 2 |
| 8a | 4 | 4 | 0.5 |
| 8b | 8 | 8 | 2 |
| 9a | 16 | 8 | 2 |
| 9b | 8 | 4 | 2 |

Antimicrobial activity was also tested in vivo using the Murine Assay procedure. Groups of female mice (six mice weighing 18–20 grams each) were injected intraperitoneally with bacteria which were thawed just prior to use and suspended in brain heart infusion with 4% brewers yeast (*Staphylococcus aureus*) or brain heart infusion (Streptococcus species). Antibiotic treatment at six dose levels per drug was administered one hour and five hours after infection by either oral intubation or subcutaneous routes. Survival was observed daily for six days. $ED_{50}$ values based on mortality ratios were calculated using probit analysis. The subject compounds were compared against well-known antimicrobial (vancomycin) as controls. The data are shown in TABLE 2.

TABLE 2

In Vivo Activity of Compounds Against *S. aureus* UC® No. 9213

| Example No. | $Ed_{50}$ (μg/mL) | Vancomycin $ED_{50}$ (μg/mL) |
|---|---|---|
| 1 | >20 | 3.0 |
| 3 | 5.8 | 1.6 |
| 4 | >20 | 4.0 |
| 5 | 8.6 | 1.6 |

In order to more fully illustrate the nature of the invention and the manner of practicing the same, the following experimental examples are presented, but they should not be taken as limiting.

EXAMPLE 1

Preparation of 8-[5-(S)-[(acetylamino)methyl]-2-oxo-3-oxazolidinyl]-1,2,4a,5-tetrahydropyrazino[2,1-c][1,4]benzoxazine-3(4H)-carboxylic acid phenylmethyl ester Step 1
Preparation of (±)-N,N'-Dibenzyloxycarbonylpiperazine-2-carboxylic acid
2-Pyrazinecarboxylic acid (2.15 g, 17.32 mmol) is placed in a hydrogenation bottle containing water (100 mL), sodium bicarbonate (1.45 g, 17.32 mmol) and palladium black (500 mg). The bottle is placed under hydrogen (40 p.s.i.) for 60 hours, filtered through celite and lyophilized. The residue is dissolved in water (25 mL), cooled to 0° C., and treated with sodium bicarbonate (3.78 g, 45.00 mmol) and benzyloxycarbonylchloride (6.25 mL, 41.60 mmol) in acetone (25 mL). After stirring 20 hours at ambient temperature, the acetone is removed in vacuo and the mixture is partitioned between methylene chloride (200 mL) and water (50 mL). The pH of the aqueous phase is adjusted to 2 with 1N HCl. The organic phase is washed with saline, dried over $MgSO_4$, and concentrated in vacuo to give the title compound, MS (CI, $NH_3$) m/z 416 $[M+NH_4]^+$.

Step 2

Preparation of (±)-Methyl N,N'-dibenzyloxycarbonyl-piperazine-2-carboxylate.

To a flask containing N,N'-dibenzyloxycarbonyl-piperazine-2-carboxylic acid (Step 1, 12.83 g, 32.20 mmol) dissolved in dry DMF (50 mL) is added methyl iodide (5.6 mL, 90.00 mmol) and potassium carbonate (4.60 g, 32.20 mmol). The mixture is stirred for 4 hours at ambient temperature under an inert atmosphere. The reaction is concentrated in vacuo, diluted with ethyl acetate (150 mL), washed with water (3×50 mL) and saline, dried over $MgSO_4$, concentrated in vacuo, and chromatographed on silica gel (70–230 mesh), eluting with hexane/ethyl acetate (50/50). The appropriate fractions are combined ($R_f$=0.55, TLC, hexane/ethyl acetate, 50/50) and concentrated in vacuo to give the title compound, NMR (CDCl) 7.31, 5.15, 5.12, 4.70, 4.1–2.9.

Step 3:

Preparation of (±)-Tetrahydro-3-oxo-3H-oxazolo(3, 4-a)pyrazin-7(1H)-carboxylic acid phenylmethylester.

To a flask containing methyl N,N'-dibenzyl-oxycarbonylpiperazine-2-carboxylate (Step 2, 12.60 g, 30.60 mmol) and tetrahydrofuran (65 mL) at 0° C. under an inert atmosphere is added lithium borohydride (2 M in THF) (23.00 mL, 45.9 mmol). The solution is warmed to ambient temperature, stirred 19 hours, cooled to 0° C., and quenched with water (50 mL). The mixture is diluted with ethyl acetate (100 mL) and the pH is adjusted to 2 with 1N HCl. The layers are separated and the aqueous phase is extracted with ethyl acetate (50 mL). The organics are combined, washed with water (50 mL) and saline, dried over $MgSO_4$, concentrated in vacuo, and chromatographed on silica gel (70–230 mesh, 500 g), eluting with hexane/ethyl acetate (50/50) then ethyl acetate (100). The appropriate fractions are combined ($R_f$=0.17, TLC, hexane/ethyl acetate, 50/50) and concentrated in vacuo to give the title compound, mp 85.5–86.5° C.

Step 4

Preparation of (±)-3-Hydroxymethylpiperazine-1-carboxylic acid phenylmethylester.

To a flame dried flask under an inert atmosphere containing potassium tert-butoxide (12.18 g, 108.58 mmol) and water (900 mg, 50.00 mmol) at 0° C. is added (±)-tetrahydro-3-oxo-3H-oxazolo(3,4-a)pyrazin-7(1H)-carboxylic acid phenylmethylester (Step 3, 10.00 g, 36.19 mmol). The reaction is warmed to ambient temperature, stirred for 2 hours, cooled to 0° C., acidified to pH=2 with conc. HCl, adjusted to pH=9 with 1N NaOH, and extracted with methylene chloride (2×100 mL). The organic extracts are combined, dried over $Na_2SO_4$, concentrated in vacuo, and chromatographed on silica gel (230–400 mesh, 250 mL), eluting with chloroform/methanol (95/5). The appropriate fractions are combined ($R_f$=0.13, TLC, chloroform/methanol, 90/10) and concentrated in vacuo to give the title compound, NMR (CDCl$_3$) 7.34–7.25, 5.09, 3.95, 3.55–3.53, 3.41, 3.34, 2.92, 2.72–2.70.

Step 5

Preparation of (±)-4-(2-Fluoro-4-nitrophen-1-yl)-3-hydroxymethylpiperazine-1-carboxylic acid phenylmethylester.

To a flame dried flask under an inert atmosphere containing (±)-3-hydroxymethylpiperazine-1-carboxylic acid phenylmethylester (Step 4, 6.00 g, 23.97 mmol) in DMSO (150 mL) and $K_2HPO_4$ (16.70 g, 95.88 mmol) is added 3,4-difluoronitrobenzene (5.31 mL, 47.94 mmol) and heated to 90° C. for 24 hours. The reaction is cooled to ambient temperature, concentrated in vacuo, and diluted with methylene chloride (200 mL) and water (150 mL). The layers are separated and the aqueous phase is extracted with methylene chloride (4×100 mL). The organic extracts are combined, washed with saline, dried over $Na_2SO_4$, concentrated in vacuo, and chromatographed on silica gel (230–400 mesh, 500 mL), eluting with chloroform/methanol (99.5/0.5). The appropriate fractions are combined ($R_f$=0.05, TLC, hexane/ethyl acetate, 75/25) and concentrated in vacuo to give the title compound, NMR (CDCl$_3$) 7.82, 7.73, 7.30–7.25, 6.87, 5.09, 4.16–4.07, 3.92, 3.65, 3.32–3.24.

Step 6

Preparation of 1,2,4a,5-Tetrahydro-8-nitro-pyrazino[2,1-c][1,4]benzoxazine-3(4H)-carboxylic acid phenylmethyl ester.

To a flame dried flask under an inert atmosphere containing (±)-4-(2-fluoro-4-nitrophen-1-yl)-3-hydroxymethylpiperazine-1-carboxylic acid phenylmethylester (Step 5, 9.15 g, 23.50 mmol) in DMF (200 mL) at 0° C. is added sodium hydride (60% dispersion in mineral oil) (1.41 g, 35.25 mmol) and stirred at ambient temperature for 24 hours. The reaction is quenched with water (100 mL), conc in vacuo, diluted with ethyl acetate (100 mL) and water (100 mL). The layers are separated and the aqueous phase is extracted with ethyl acetate (5×200 mL). The organic extracts are combined, washed with saline, dried over $Na_2SO_4$, concentrated in vacuo, and chromatographed on silica gel (230–400 mesh, 500 mL), eluting with hexane/ethyl acetate (75/25). The appropriate fractions are combined ($R_f$=0.47, TLC, hexane/ethyl acetate, 50/50) and concentrated in vacuo to give the title compound, mp 138–140° C.

Step 7

Preparation of (±)-8-[[(Phenylmethoxy)carbonyl]amino]-pyrazino [2,1-c][1,4]benzoxazine-3(4H)-carboxylic acid phenylmethyl ester.

To a flask containing 1,2,4a,5-tetrahydro-8-nitro-pyrazino [2,1-c][1,4]benzoxazine-3(4H)-carboxylic acid phenylmethyl ester (Step 6, 2.75 g, 7.45 mmol) in tetrahydrofuran (100 mL) and methanol (50 mL) is added 10% palladium on carbon (2.00 g) and ammonium formate (4.69 g, 74.45 mmol), heated to reflux for 2 hours and stirred at ambient temperature for 15 hours. The mixture is filtered through celite and concentrated in vacuo. To the residue dissolved in water (15 mL) and acetone (15 mL) cooled to 0° C. is added potassium carbonate (2.27 g, 16.39 mmol) followed by benzyloxycarbonylchloride (2.34 mL, 16.39 mmol). The reaction is slowly warmed to ambient temperature, stirred for 64 hours, concentrated in vacuo, diluted with ethyl acetate (100 mL), washed with water (2×25 mL) and saline, dried over $Na_2SO_4$, concentrated in vacuo and chromatographed on silica gel (230–400 mesh, 200 mL), eluting with hexane/ethyl acetate (75/25). The appropriate fractions are combined ($R_f$=0.46, TLC, hexane/ethyl acetate, 50/50) and concentrated in vacuo to give the title compound, mp 118–120° C.

Step 8
Preparation of 1,2,4a,5-Tetrahydro-8-[5-(R)-(hydroxymethyl)-2-oxo-3-oxazolidinyl]-pyrazino[2,1-c][1,4]benzoxazine-3(4H)-carboxylic acid phenylmethyl ester.

To a flame dried flask under an inert atmosphere containing 8-[[(phenylmethoxy)carbonyl]amino]-pyrazino[2,1-c][1,4]benzoxazine-3(4H)-carboxylic acid phenylmethyl ester (Step 7, 1.00 g, 2.11 mmol) in tetrahydrofuran (20 mL) cooled to −78° C. is added n-butyl lithium (1.6M in hexanes) (1.39 mL, 2.22 mmol) followed by (R)-glycidyl butyrate (0.33 mL, 2.32 mmol). The reaction is stirred 15 hours and quenched with saturated ammonium chloride (20 mL). The aqueous phase is separated and extracted with ethyl acetate (2×20 mL). The organics are combined, washed with saline, dried over $Na_2SO_4$, concentrated in vacuo, and chromatographed on silica gel (230–400 mesh, 200 mL), eluting with chloroform/methanol (99/1). The appropriate fractions are combined ($R_f$=0.16, TLC, chloroform/methanol, 95/5) and concentrated in vacuo to give the title compound, NMR ($CDCl_3$) 7.39–7.31, 7.04, 6.96, 6.75, 5.16, 4.68, 4.20–3.99, 4.15, 3.96–3.86, 3.73–3.62, 3.16–2.97, 2.82–2.66.

Step 9
Preparation of 8-[5-(S)-[(Acetylamino)methyl]-2-oxo-3-oxazolidinyl]-1,2,4a,5-tetrahydropyrazino[2,1-c][1,4]benzoxazine-3(4H) -carboxylic acid phenylmethyl ester.

To a flame dried flask under an inert atmosphere containing 1,2,4a,5-tetrahydro-8-[5-(R)-(hydroxymethyl)-2-oxo-3-oxazolidinyl]-pyrazino[2,1-c][1,4]benzoxazine-3(4H)-carboxylic acid phenylmethyl ester analog (Step 8, 650 mg, 1.47 mmol) in methylene chloride (20 mL) cooled to 0° C is added triethylamine (0.31 mL, 2.20 mmol) and methanesulfonyl chloride (0.12 mL, 1.34 mmol) followed by warming 35 to ambient temperature. After 2 hours, the organic phase is washed with water (10 mL), saturated $NaHCO_3$ (10 mL) and saline, dried over $Na_2SO_4$, and concentrated in vacuo. The residue is transferred to a resealable tube and diluted with tetrahydrofuran (2 mL), isopropanol (2 mL), and conc. ammonium hydroxide (2 mL). The solution is sealed and heated to 100° C. for 15 hours. The tubes contents are diluted with ethyl acetate (50 mL), washed with saline, dried over $Na_2SO_4$, and concentrated in vacuo. The residue is transferred to a flask containing methylene chloride (15 mL), cooled to 0° C., and pyridine (0.32 mL, 3.94 mmol) and acetic anhydride (0.16 mL, 1.64 mmol) are added. The reaction is stirred 15 hours, diluted with methylene chloride (50 mL), washed with 1N HCl (20 mL), saturated $NaHCO_3$ (20 mL), and saline, dried over $Na_2SO_4$, concentrated in vacuo and chromatographed on silica gel (230–400 mesh, 100 mL), eluting with chloroform/methanol (99/1). The appropriate fractions are combined ($R_f$=0.22, TLC, chloroform/methanol, 95/5) and concentrated in vacuo to give the title compound, HRMS calcd for $C_{25}H_{28}N_4O_6$: 480.2009. Found: 480.2034.

EXAMPLE 2

Preparation of N-[[3-[1,2,3,4,4a,5-hexahydro-3-[(phenylmethoxy)acetyl]pyrazino [2,1-c][1,4]benzoxazin-8-yl]-2-oxo-5-(S) -oxazolidinyl]methyl]-acetamide.

To a flask containing 8-[5-(S)-[(acetylamino)methyl]-2-oxo-3-oxazolidinyl]-1,2,4a, 5-tetrahydropyrazino[2,1-c][1,4]benzoxazine-3(4H)-carboxylic acid phenylmethyl ester (EXAMPLE 1, 150 mg, 0.31 mmol) in methanol (5 mL) and methylene chloride (5 mL) is introduced 10% palladium on carbon (70 mg). The mixture is placed under a hydrogen balloon for 17 hours, filtered through celite, and concentrated in vacuo. The residue is dissolved in methylene chloride (10 mL) and triethylamine (0.09 mL, 0.62 mmol) and benzyloxyacetyl chloride (0.06 mL, 0.40 mmol) are added at 0° C. under an inert atmosphere. The reaction is warmed to ambient temperature, stirred for 15 hours, washed with water (10 mL) and saline, concentrated in vacuo, and chromatographed on silica gel (230–400 mesh, 100 mL), eluting with chloroform/methanol (96/4). The appropriate fractions are combined ($R_f$=0.46, TLC, chloroform/methanol, 90/10) and concentrated in vacuo to give the title compound, NMR (CDCl3) 7.36–7.29, 6.96–6.94, 6.85, 6.70, 4.69, 4.60, 4.50, 4.23–4.15, 3.97–3.91, 3.70–3.52, 3.27, 2.99, 2.82, 2.65, 2.44, 1.98.

EXAMPLE 3

Preparation of 8-[5-(S)-[(acetylamino)methyl]-2-oxo-3 oxazolidinyl]-1,2,4a,5-tetrahydropyrazino[2,1-c][1,4]benzoxazine-3(4H)-carboxylic acid methyl ester.

Following the general procedure of EXAMPLE 2 and making noncritical variations but substituting methyl chloroformate (0.04 mL, 0.47 mmol) for benzyloxyacetyl chloride, the title compound is obtained, mp 185–190° C.

EXAMPLE 4

Preparation of N-[[3-[1,2,3,4,4a,5-hexahydro-3-(hydroxyacetyl)pyrazino [2,1-c][1,4]benzoxazin-8-yl]-2-oxo-5-(S)-oxazolidinyl]methylacetamide.

In a manner similar to EXAMPLE 2 and making any non-critical changes, but substituting acetoxyacetyl chloride (0.04 mL, 0.40 mmol) for benzyloxyacetyl chloride, N-[[3-[3-[(acetoxy)acetyl]-1,2,3,4,4a,5-hexahydropyrazino[2,1-c][1,4]benzoxazin -8-yl]-2-oxo-5-(S)-oxazolidinyl]methyl]-acetamide is obtained. The residue is dissolved in methanol (15 mL) and potassium carbonate (140 mg, 0.98 mmol) is added. The reaction is stirred 15 hours, concentrated in vacuo, and chromatograph on silica gel (230–400 mesh, 100 mL), eluting with chloroform/methanol (95/5). The appropriate fractions are combined ($R_f$=0.21, TLC, chloroform/methanol, 90/10) and concentrated in vacuo to give the title compound, mp 115–118° C.

EXAMPLE 5

Preparation of N-[[3-[1,2,3,4,4a,5-hexahydro-3-(5 isoxazolylcarbonyl)pyrazino[2,1-c][1,4]benzoxazin-8-yl]-2-oxo-5-(S) -oxazolidinyl]methyl]-acetamide.

To a flask containing 8-[5-(S)-[(acetylamino)methyl]-2-oxo-3-oxazolidinyl]-1,2,4a, 5-tetrahydropyrazino[2,1-c][1,4]benzoxazine-3(4H)-carboxylic acid phenylmethyl ester (EXAMPLE 1, 150 mg, 0.31 mmol) in methanol (5 mL) and methylene chloride (5 mL) is introduced 10% palladium on carbon (70 mg). The mixture is placed under a hydrogen balloon for 17 hours, filtered through celite, and concentrated in vacuo. The residue is dissolved in pyridine (5 mL) followed by the addition of isoxazole-5-carboxylic acid (40 mg, 0.35 mmol), 4-dimethylaminopyridine (5 mg, 0.04 mmol), and 1-ethyl-3-(3-dimethylaminopropyl) carbodiimide hydrochloride(70 mg, 0.35 mmol). The reaction is stirred under an inert atmosphere for 17 hours, diluted with methylene chloride (20 mL), washed with 1N HCl (20 mL) and saline, dried over $Na_2SO_4$, concentrated in vacuo and chromatographed on silica gel (230–400 mesh, 100 mL), eluting with chloroform/methanol (97/3). The appropriate fractions are combined ($R_f$=0.42, TLC, chloroform/methanol, 90/10) and concentrated in vacuo to give the title compound, HRMS calcd for $C_{21}H_{23}N_5O_6$: 441.1648. Found: 441.1658.

EXAMPLE 6

Preparation of N-[[3-[1,2,3,4,4a,5-hexahydro-3-(1H-indol-2-ylcarbonyl)pyrazino[2,1-c][1,4]benzoxazin-8-yl]-2-oxo-5-(S)-oxazolidinyl]methyl]-acetamide.

Following the general procedure of EXAMPLE 5 and making noncritical variations but substituting indole-2-carboxylic acid (60 mg, 0.35 mmol) for isoxazole -5-carboxylic acid the title compound is obtained, mp >250° C.

EXAMPLE 7

Preparation of (R)-8-[5-(S)-[(acetylamino)methyl]-2-oxo-3-oxazolidinyl]-1,2,4a,5-tetrahydropyrazino [2,1-c][1,4]benzoxazin-3(4H)-carboxylic acid phenylmethyl ester (7a) and (S)-8-[5-(S)-[(acetylamino)methyl]-2-oxo-3-oxazolidinyl]-1,2,4a, 5-tetrahydropyrazino[2,1-c][1,4]benzoxazin-3(4H)-carboxylic acid phenylmethyl ester (7b).

Step 1

Preparation of (R) and (S)-1,2,4a,5-Tetrahydro-8-[5-(R)-(hydroxymethyl)-2-oxo-3-oxazolidinyl]-pyrazino[2,1-c][1, 4]benzoxazine -3(4H)-carboxylic acid phenylmethyl ester.

A solution of 50 mg/mL of a mixture of diastereomers 1,2,4a,5-Tetrahydro-8-[5-(R)-(hydroxymethyl)-2-oxo-3-oxazolidinyl]-pyrazino[2,1-c][1,4]benzoxazine-3(4H) -carboxylic acid phenylmethyl ester (EXAMPLE 1, Step 8) is made in the mobile phase that consisted of 35% EtOH in hexane (V/V). The solution (200 mg) is injected into a 5.1×50 cm Chiralcel OD column at 30° C. The column is eluted at 45 ml/min and monitored at 305 nm. The two diastereomers are collected using a peak recognition program and fractions are pooled appropriately. Each diastereomer is obtained at >98% diastereomer excess. Diastereomeric excess is determined on a 0.46×25 cm Chiralcel OD-H column at ambient column temperature, using the mobile phase consisted of 0.1% TEA in EtOH and the monitor set at 218 nm detection. The retention times are 58.9 and 65.6 minutes. ($\alpha$=1.14; 0.2 mL/min).

Step 2

Preparation of (R) and (S) -N-[[3-[1,2,3,4,4a,5-hexahydro-3-[(phenylmethoxy)acetyl]pyrazino[2,1-c][1,4]benzoxazin-8-yl]-2-oxo-5-(S)-oxazolidinyl]methyl]-acetamide.

Following the general procedure of EXAMPLE 1, Step 9 and EXAMPLE 2 and making noncritical variations but using the products of EXAMPLE 7, Step 1, the title compounds are obtained. HRMS calcd for $C_{25}H_{28}N_4O_6$: 480.2009. Found: 480.2007 (7a); HRMS calcd for $C_{25}H_{28}$, $N_4O_6$: 480.2009. Found: 480.1993 (7b).

EXAMPLE 8

Preparation of (R)-8-[5-(S)-[(acetylamino)methyl]-2-oxo-3 -oxazolidinyl)-1,2,4a,5-tetrahydropyrazino [2,1-c][1,4]benzoxazine-3(4H)-carboxylic acid methyl ester (8a) and (S)-8-[5-(S)-[(acetylamino) methyl]-2-oxo-3-oxazolidinyl]-1,2, 4a,5-tetrahydropyrazino[2,1-c][1,4]benzoxazine-3(4H)-carboxylic acid methyl ester (8b).

Following the general procedure of EXAMPLE 3 and making noncritical variations but using the products of EXAMPLE 7, the title compounds are obtained.

Anal. Calcd for $C_{19}H_{24}N_4O_6$: C, 56.43; H, 5.98; N, 13.85. Found: C, 56.42; H, 6.11; N, 13.71 (8a); Anal. Calcd for $C_{19}H_{24}N_4O_6$: C, 56.43; H, 5.98; N, 13.85. Found: C, 56.19; H, 5.94; N, 13.58 (8b).

EXAMPLE 9

Preparation of (R)-N-[[[1,2,3,4,4a,5-hexahydropyridino[2,1-c][1,4]benzoxazin-8-yl]-2-oxo-5-(S)-oxazolidinyl]methyl]-acetamide (9a) and (S)-N-[[[1,2,3,4,4a,5-hexahydropyridino[2,1-c][1,4] benzoxazin-8-yl]-2-oxo-5-(S)-oxazolidinyl]methyl]-acetamide (9b).

Step 1

Preparation of 3-fluoro-4-[2-(S)-[hydroxymethyl]piperidin-1-yl]]nitrobenzene and 3-fluoro-4-[2-(R)-[hydroxymethyl] piperidin-1-yl]]nitrobenzene Following the general procedure of EXAMPLE 1, Step 5 and making noncritical variations but substituting 2-[hydroxymethyl]piperidine (commercially available) for (±)-3-hydroxymethylpiperazine-1-carboxylic acid phenylmethylester, the title compounds are obtained as a mixture of two enantiomers.

Step 2

Preparation of 3-fluoro-4-[2-(S)-[hydroxymethyl]piperidin-1-yl]]nitrobenzene and 3-fluoro-4-[2-(R)-[hydroxymethyl] piperidin-1-yl]]nitrobenzene.

A solution of 50 mg/mL of a mixture of enantiomers is made in the mobile phase that consisted of 5% IPA in hexane (V/V). The solution (55 mg) is injected into a 2×25 cm Chiralcel AD column at 30° C. The column is eluted at 10×15 ml/min and monitored at 370 nm. The two enantiomers are collected using a peak recognition program and fractions are pooled appropriately. Each enantiomer is obtained at >97% enantiomer excess. Enantiomeric excess is determined on a 0.46×25 cm Chiralcel AD column at ambient column temperature, using the mobile phase consisting of 10% IPA in hexane and the monitor set at 370 nm detection. The retention times are 28 and 36 minutes. ($\alpha$=1.37; 0.5 mL/min).

Step 3

Preparation of (R)-N-[[[1,2,3,4,4a,5-hexahydropyridino[2, 1-c][1,4]benzoxazin-8-yl]-2-oxo-5-(S)-oxazolidinyl] methyl]-acetamide (9a) and (S)-N-[[[1,2,3,4,4a,5-hexahydropyridino[2,1-c][1,4]benzoxazin-8-yl]-2-oxo-5-(S)-oxazolidinyl ]-methyl]-acetamide (9b).

Following the general procedure of EXAMPLE 1, Steps 5-9 and making noncritical variations but using the products of EXAMPLE 9, Step 2, the title compounds are obtained. mp 227–228° C. (9a); mp 211–213° C. (9b).

SCHEME I
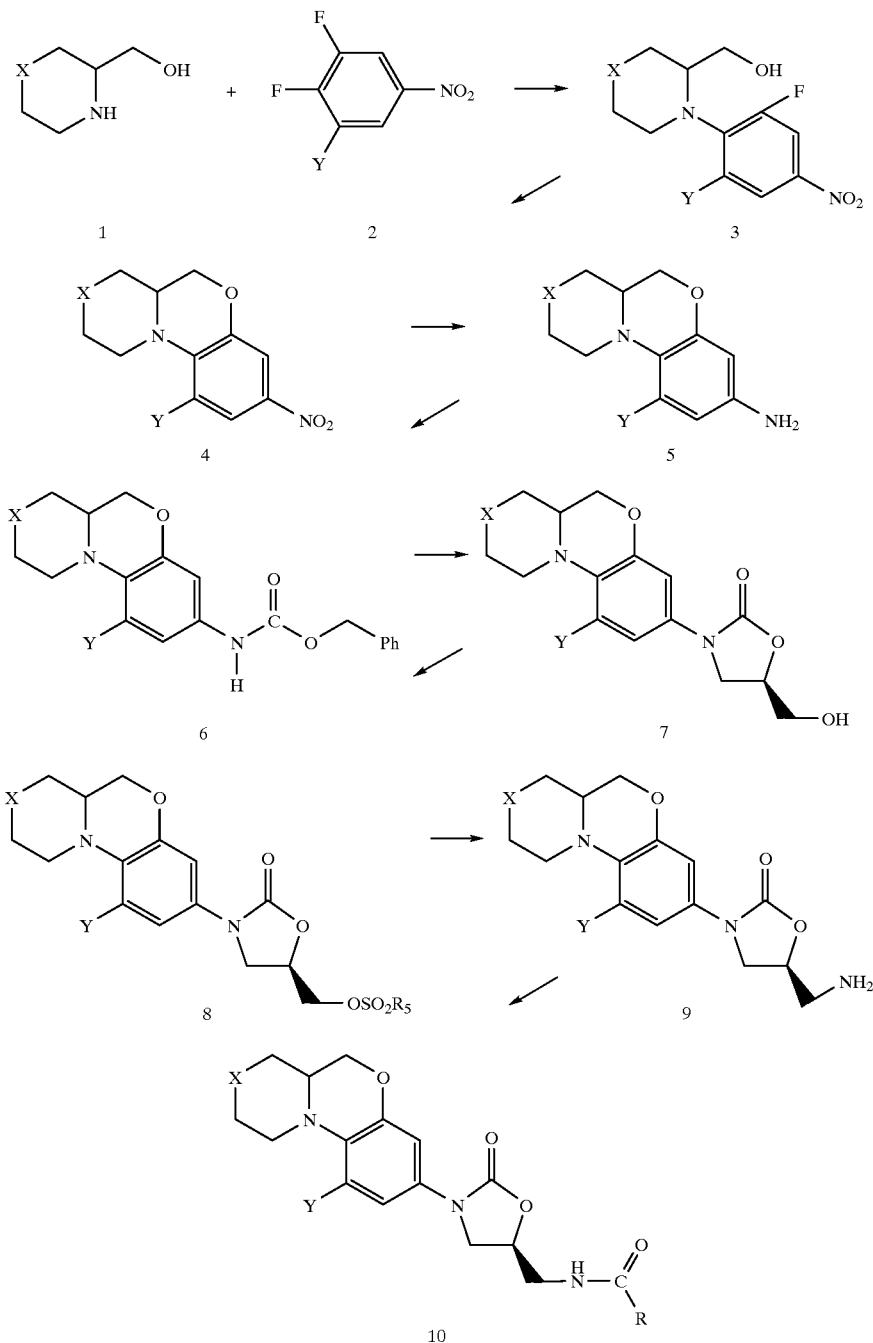
SCHEME II
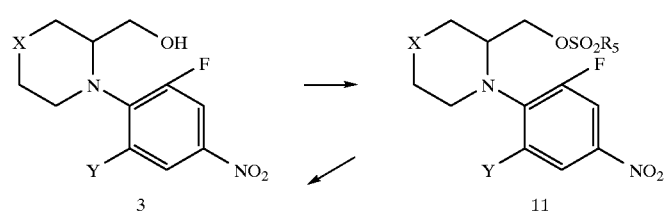

-continued
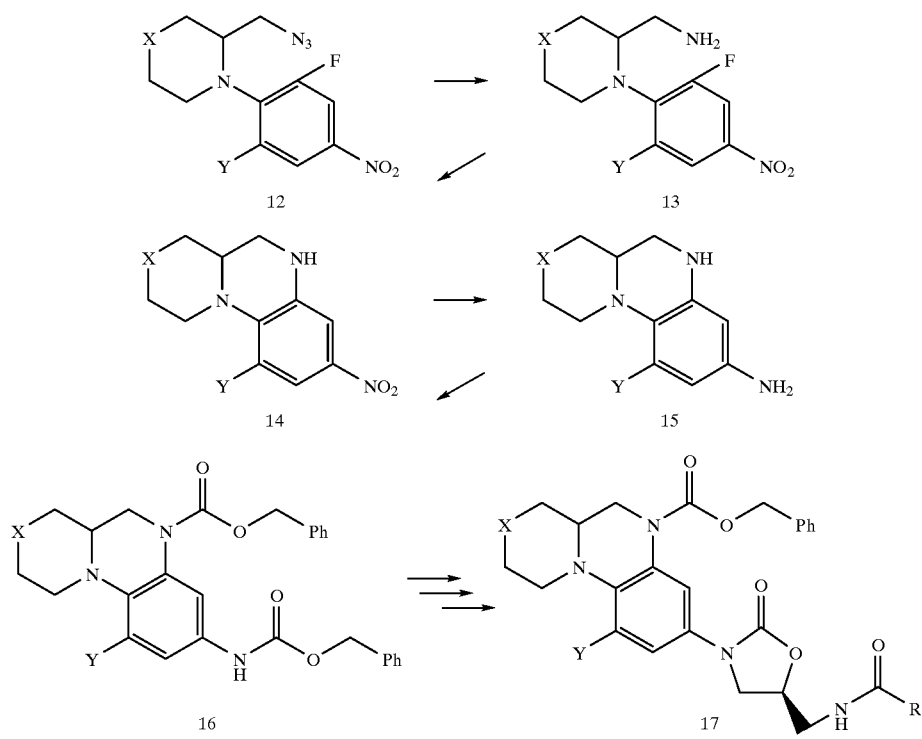
SCHEME III
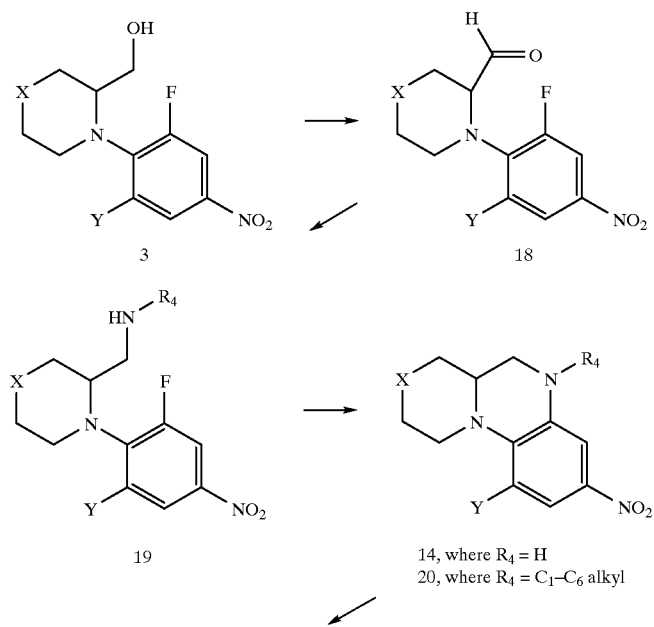
14, where R₄ = H
20, where R₄ = C₁–C₆ alkyl -continued
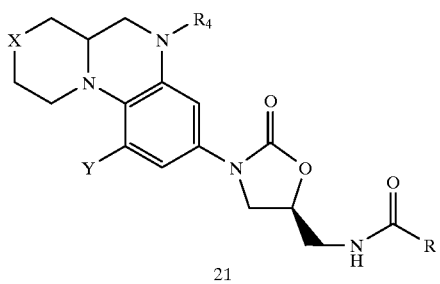
SCHEME IV
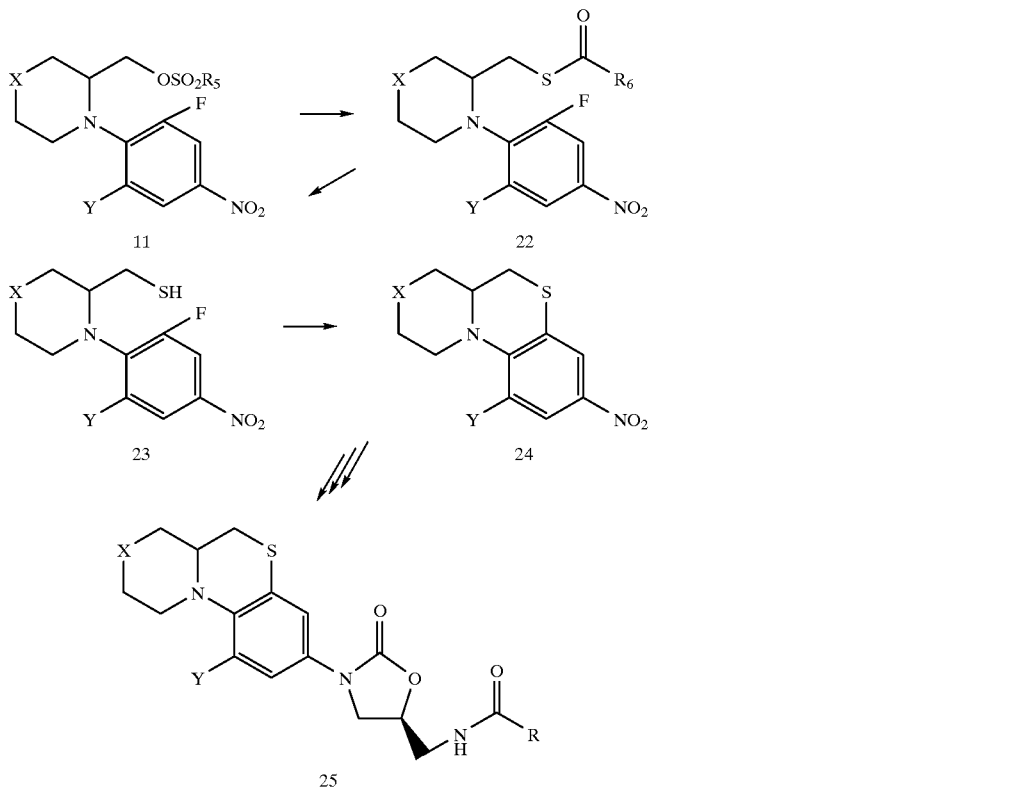
We claim:
1. A compound of the formula (I):
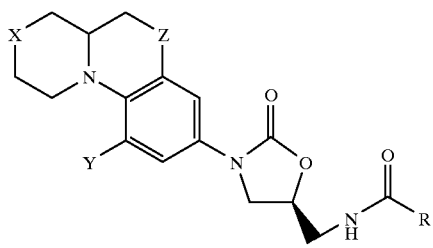
or pharmaceutical acceptable salts thereof wherein
X is S, SO, SO$_2$;
Z is
(a) NR$_4$,
(b) S, SO, SO$_2$, or
(c) O;
R$_4$ is
(a) H,
(b) C$_{1-6}$ alkyl
(c) —C(=O)—R$_{4a}$,
(d) —C(=O)—OR$_{4a}$, or
(e) —C(=O)—(CH$_2$)$_h$—C(=O)R$_{4a}$;
R$_{4a}$ is
(a) H,
(b) C$_{1-6}$ alkyl,
(c) —(CH$_2$)$_h$-Aryl, or
(d) —(CH$_2$)$_h$—OR$_{4b}$;
R$_{4b}$ is
(a) H,
(b) C$_{1-6}$ alkyl, or
(c) —(CH$_2$)$_h$-Aryl;
Y is
a) H, or b) halogen;
R is
  a) H,
  b) $C_{1-4}$ alkyl,
  c) $C_{3-6}$ cycloalkyl,
  d) $C_{1-4}$ alkoxy,
  e) amino,
  d) $C_{1-4}$ alkylamino, or
  e) $C_{1-4}$ dialkylamino;
h is 1, 2, 3, or 4; and
$C_{1-6}$ alkyl, in each of the above definitions, may be each and independently substituted with one or more halogen, hydroxy, or cyano.

2. The compound of claim 1 wherein Y is H or F.

3. The compound of claim 1 wherein R is methyl.

4. The compound of claim 1 which is an optically pure enantiomer having the S-configuration at C5 of the oxazolidinone ring.

5. A method for treating bacterial infections in patients comprising:

administering to a patient in need thereof an effective amount of a compound of Formula I as shown in claim 1.

6. The method of claim 5 wherein said compound of Formula I is administered orally, parenterally or topically in a pharmaceutical composition.

7. The method of claim 5 wherein said compound is administered in an amount of from about 0.1 to about 100 mg/kg of body weight/day.

8. A pharmaceutical composition comprising a compound of claim 1 and pharmaceutically acceptable carrier.

* * * * *